US010732592B2

(12) United States Patent
Li et al.

(10) Patent No.: US 10,732,592 B2
(45) Date of Patent: Aug. 4, 2020

(54) METHOD AND DEVICE FOR CONTROLLING TARGET MASSAGE EQUIPMENT

(71) Applicant: Beijing Xiaomi Mobile Software Co., Ltd., Beijing (CN)

(72) Inventors: Junjie Li, Beijing (CN); Gang Wang, Beijing (CN); Xiangyang Zhang, Beijing (CN)

(73) Assignee: Beijing Xiaomi Mobile Software Co., Ltd., Beijing (CN)

( * ) Notice: Subject to any disclaimer, the term of this patent is extended or adjusted under 35 U.S.C. 154(b) by 667 days.

(21) Appl. No.: 15/428,685

(22) Filed: Feb. 9, 2017

(65) Prior Publication Data

US 2017/0308046 A1 Oct. 26, 2017

(30) Foreign Application Priority Data

Apr. 21, 2016 (CN) .......................... 2016 1 0252504

(51) Int. Cl.
*G05B 19/042* (2006.01)
*G16H 20/30* (2018.01)
(Continued)

(52) U.S. Cl.
CPC ............ *G05B 19/042* (2013.01); *A61H 7/00* (2013.01); *A63B 24/0062* (2013.01);
(Continued)

(58) Field of Classification Search
CPC .............. A61H 7/00; A61H 2201/0149; A61H 2201/501; A61H 2201/5028;
(Continued)

(56) References Cited

U.S. PATENT DOCUMENTS 10,226,396 B2 * 3/2019 Ashby .................... A61H 7/007
10,264,997 B1 * 4/2019 Romrell ................ A61B 5/1118
(Continued)

FOREIGN PATENT DOCUMENTS

CN 1623527 A 6/2005
CN 103876721 A 6/2014
(Continued)

OTHER PUBLICATIONS

First Office Action issued by the State Intellectual Property Office of the People's Republic of China (SIPO) dated Jul. 28, 2017, in counterpart Chinese Application No. 201610252504.1.
(Continued)

*Primary Examiner* — Tu A Vo
*Assistant Examiner* — Alexander Morales
(74) *Attorney, Agent, or Firm* — Finnegan, Henderson, Farabow, Garrett & Dunner, L.L.P.

(57) ABSTRACT

A method for controlling target massage equipment, a device for controlling the target massage equipment, and a non-transitory computer readable storage medium. The method includes obtaining at least one of an arm swing frequency or a total exercise intensity when a user is doing exercise through a wearable device, obtaining exercise information according to the at least one of the arm swing frequency or the total exercise intensity, and controlling the target massage equipment to operate according to the exercise information.

18 Claims, 13 Drawing Sheets

(51) Int. Cl.
*A61H 7/00* (2006.01)
*A63B 24/00* (2006.01)

(52) U.S. Cl.
CPC ..... *G16H 20/30* (2018.01); *A61H 2201/0149* (2013.01); *A61H 2201/501* (2013.01); *A61H 2201/5028* (2013.01); *A61H 2201/5046* (2013.01); *A61H 2201/5058* (2013.01); *A61H 2201/5061* (2013.01); *A61H 2201/5084* (2013.01); *A61H 2201/5097* (2013.01); *A63B 2024/0068* (2013.01); *A63B 2220/836* (2013.01); *A63B 2230/045* (2013.01); *G05B 2219/25208* (2013.01)

(58) Field of Classification Search
CPC .... A61H 2201/5046; A61H 2201/5058; A61H 2201/5061; A61H 2201/5084; A61H 2201/5097; A63B 24/0062; A63B 2024/0068; A63B 2220/836; A63B 2220/045; G05B 19/042; G05B 2219/25208; G16H 20/30
USPC ................................................ 482/1, 4, 8, 9
See application file for complete search history.

(56) References Cited

U.S. PATENT DOCUMENTS

| | | | | |
|---|---|---|---|---|
| 2005/0113723 | A1 | 5/2005 | Ueyama et al. | |
| 2005/0131273 | A1* | 6/2005 | Asano | A61M 21/00 600/27 |
| 2008/0048384 | A1 | 2/2008 | Matsubara et al. | |
| 2009/0177128 | A1* | 7/2009 | Fukuyama | A61H 7/001 601/98 |
| 2015/0099945 | A1 | 4/2015 | Hawkins, III et al. | |
| 2015/0143601 | A1 | 5/2015 | Longinotti-Buitoni et al. | |
| 2015/0199494 | A1* | 7/2015 | Koduri | G06F 19/3481 700/91 |
| 2015/0289217 | A1 | 10/2015 | Ban et al. | |
| 2016/0007158 | A1* | 1/2016 | Venkatraman | H04W 4/023 455/456.2 |
| 2016/0249174 | A1* | 8/2016 | Patel | G01K 13/002 |

FOREIGN PATENT DOCUMENTS

| | | | |
|---|---|---|---|
| CN | 104068862 | A | 10/2014 |
| CN | 104127188 | A | 11/2014 |
| CN | 204086862 | U | 1/2015 |
| CN | 204105955 | U | 1/2015 |
| CN | 104434121 | A | 3/2015 |
| CN | 204890567 | U | 12/2015 |
| CN | 105495839 | A | 4/2016 |
| KR | 2003-0035048 | A | 5/2003 |
| WO | WO 2015139089 | A1 | 9/2015 |

OTHER PUBLICATIONS

Extended European Search Report issued by European Patent Office dated Jun. 12, 2017, in counterpart European Application No. 16197637.8.
International Search Report and Written Opinion for International Application No. PCT/CN2016/092861 dated Dec. 28, 2016.
English translation of International Search Report for International Application No. PCT/CN2016/092861 dated Dec. 28, 2016.

* cited by examiner

METHOD AND DEVICE FOR CONTROLLING TARGET MASSAGE EQUIPMENT

CROSS-REFERENCE TO RELATED APPLICATION

This application is based upon and claims priority to Chinese Patent Application Serial No. 201610252504.1, filed with the State Intellectual Property Office of P. R. China on Apr. 21, 2016, the entire content of which is incorporated herein by reference.

TECHNICAL FIELD

The present disclosure relates to the field of massage equipment technology, and more particularly, to a method and device for controlling target massage equipment.

BACKGROUND

At present, with the development of society, an increasing number of people have developed better fitness consciousness. An effective recovery after exercise often brings a better fitness result. Thus, massage equipment is increasingly used to provide massage to help the body recover after exercise. The existing massage equipment, however, is not intelligent. The massage mode is often very simple, causing inconvenience for a user to achieve a full body recovery.

SUMMARY

Embodiments of the present disclosure provide a method and a device for controlling target massage equipment. The technical solutions will be described as follows.

According to a first aspect of the present disclosure, a method for controlling target massage equipment is provided. The method includes obtaining exercise information, and controlling the target massage equipment to operate according to the exercise information.

According to a second aspect of the present disclosure, a device for controlling target massage equipment is provided. The device includes a memory for storing instructions. The device also includes a processor configured to execute the instructions to obtain exercise information, and control the target massage equipment to operate according to the exercise information.

According to a third aspect of the present disclosure, a non-transitory computer-readable storage medium is provided. The non-transitory computer-readable storage medium has instructions stored therein that, when executed by one or more processors of a device, cause the device to perform a method for controlling target massage equipment. The method includes obtaining exercise information, and controlling the target massage equipment to operate according to the exercise information.

It should be understood that the above general descriptions and the following detail descriptions are explanatory and illustrative, and these descriptions shall not be construed to limit the present disclosure.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise specified. The implementations set forth in the following description of exemplary embodiments do not represent all implementations consistent with the disclosure. Instead, they are merely examples of devices and methods consistent with aspects of the present disclosure as recited in the appended claims.

At present, with the development of society, an increasing number of people have gained better fitness consciousness. An effective recovery after exercise often brings a better fitness result. Thus, massage equipment is increasingly used to provide massage to help the body recover after exercise. The existing massage equipment, however, is not intelligent. The massage mode is often very simple, causing inconvenience for a user to achieve a full body recovery.

In order to solve the above problems, embodiments of the present disclosure provide a method for controlling target massage equipment. The method can be applied in a control program, a system, or a device associated with the target massage equipment. The subject that executes the method can be a terminal or the target massage equipment.

Figure 1:
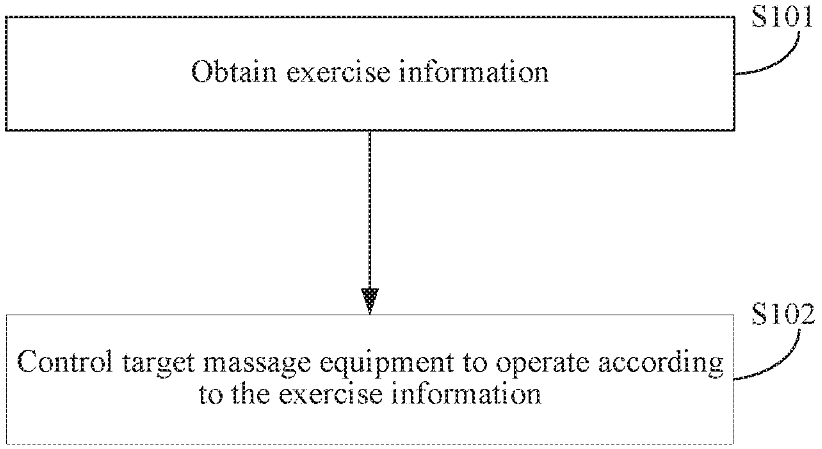
FIG. 1 shows a flowchart illustrating a method for controlling target massage equipment according to an exemplary embodiment of the present disclosure.

FIG. 1 shows a flowchart illustrating a method for controlling target massage equipment according to an exemplary embodiment of the present disclosure.

As shown in FIG. 1, the method includes steps S101 and S102.

At step S101, exercise information is obtained.

The exercise information refers to information regarding exercise or fitness activities of a user within a preset time period (such as latest week or latest N days). The exercise information includes, but is not limited to, at least one of the followings: moving body part information regarding a body part of the user that has been exercised, an exercise intensity ratio between moving body parts that have been exercised, exercise intensity information regarding the moving body parts, and information regarding exercise equipment that have been used in the exercise.

Additionally, the subject that obtains the exercise information is a terminal or the target massage equipment.

At step S102, the target massage equipment is controlled to operate according to the exercise information. When the target massage equipment is controlled to operate according to the exercise information, the target massage equipment automatically provides personalized massage service to the user according to the exercise information. Alternatively, the target massage equipment is controlled through the terminal to operate so as to provide personalized massage service to the user.

In some embodiments, an exercise status of the user is determined, with improved accuracy as compared with the existing technology, based on the obtained exercise information, such that the target massage equipment is controlled to perform a targeted movement based on the exercise information obtained when the user was exercising. By performing the targeted movement, the target massage equipment automatically provides a comfortable, suitable, and effective massage to the user based on the user's exercise information. As a result, after exercise, the body of the user can recover in a better and faster manner through an optimum massage. The disclosed method may not require the user to manually select massage modes, thereby reducing the operations that the user is required to perform.

Figure 2:
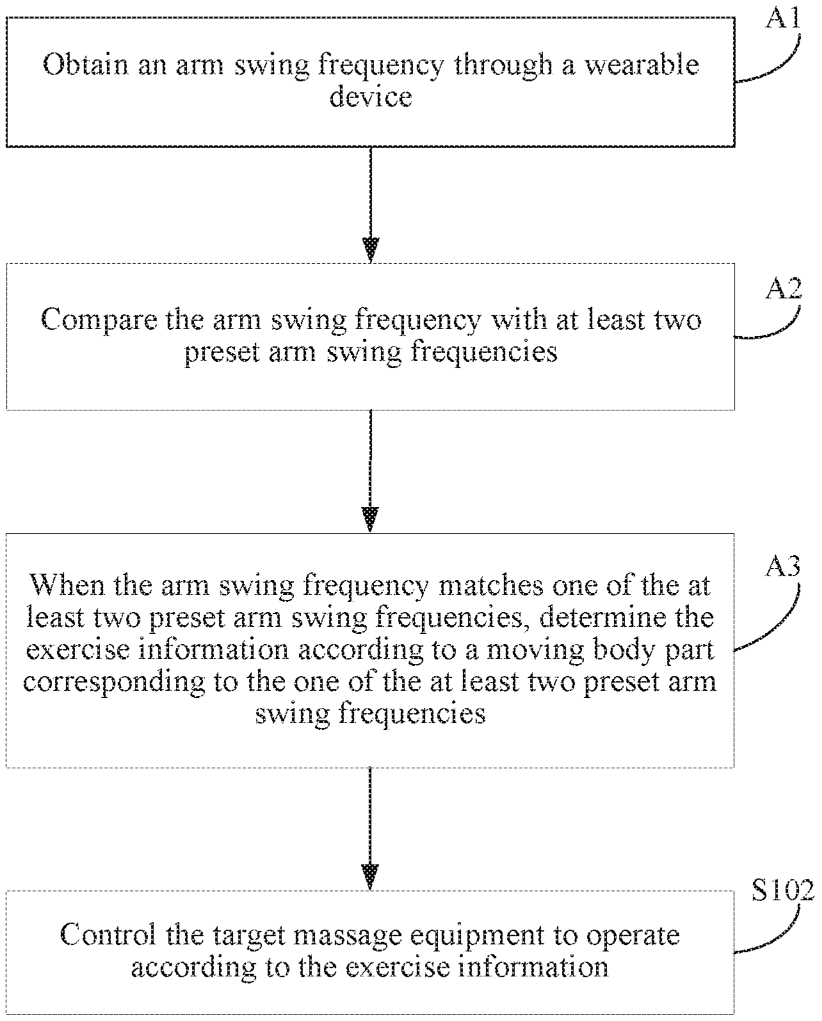
FIG. 2 shows a flowchart illustrating a method for obtaining exercise information according to an exemplary embodiment of the present disclosure.

FIG. 2 shows a flowchart illustrating a method for obtaining exercise information according to an exemplary embodiment of the present disclosure.

As shown in FIG. 2, the step S101 shown in FIG. 1 is executed as follows.

At step A1, an arm swing frequency is obtained through a wearable device. The wearable device includes at least one of a smart band or a smart watch.

Regardless of whether the exercise information is obtained by a terminal or the target massage equipment, the arm swing frequency is first obtained through a wearable device. The wearable device can be a smart band or a smart watch worn on the user's wrist. In some embodiments, the wearable device can also be a smart band worn on a user's finger. The wearable device is connected to the terminal or the target massage equipment through a suitable communication method, such as Bluetooth, infrared technology, WiFi (Wireless Fidelity, e.g., wireless local area network based on IEEE 802.11 standards), etc. The swing frequency is transmitted to the terminal or the target massage equipment, such that the terminal or the target massage equipment performs operations shown in steps A2 and A3.

At step A2, the arm swing frequency is compared with at least two preset arm swing frequencies.

At step A3, when the arm swing frequency matches one of the at least two preset arm swing frequencies, the exercise information is determined according to a moving body part corresponding to the one of the at least two preset arm swing frequencies.

Because each pre-stored preset arm swing frequency may correspond to a distinct moving body part (for example, when a user is lifting dumbbells, the arm swing frequency and the moving body part are different from those when the user is jogging), each preset arm swing frequency may correspond to distinct exercise information. Thus, by comparing the obtained arm swing frequency with the at least two preset arm swing frequencies, it is judged whether the arm swing frequency obtained in real time matches one of the at least two preset arm swing frequencies. If the arm swing frequency obtained in real time matches one of the at least two preset arm swing frequencies (for example, the arm swing frequency obtained in real time is equal to one of the at least two preset arm swing frequencies, or the difference between the real time arm swing frequency and one of the at least two preset swing frequencies is less than or equal to a preset frequency threshold), it is determined that the exercise information corresponding to the arm swing frequency obtained in real time is the same as the exercise information corresponding to the preset arm swing frequency matching the arm swing frequency obtained in real time. Therefore, the current exercise information of the user is determined according to the moving body part corresponding to the preset arm swing frequency matching the arm swing frequency obtained in real time. For example, the user's moving body part information or the like is determined according to the moving body part corresponding to the preset arm swing frequency matching the arm swing frequency obtained in real time.

In addition, because the arm swing frequency may not be a constant regardless of what kind of equipment is used or what kind of exercise intensity is applied during the user's exercise or fitness process, each of the at least two preset arm swing frequencies may have frequency fluctuation or may be represented by an arm swing frequency spectrogram. Correspondingly, the arm swing frequency obtained in real time can have frequency fluctuation or may be represented by an arm swing frequency spectrogram. Thus, in some embodiments, comparing the arm swing frequency obtained in real time with each of the at least two preset arm swing frequencies includes obtaining a similarity between two arm swing frequency spectrograms respectively associated with the arm swing frequency obtained in real time and one of the at least two preset arm swing frequencies. If the similarity is higher than a preset similarity (e.g., 90%), the exercise information is determined according to a preset swing frequency spectrogram that has a similarity higher than the preset similarity.

Additionally, in some embodiments, each of the at least two preset arm swing frequencies includes an arm swing frequency in the vertical direction and an arm swing frequency in the horizontal direction. In such embodiments, when comparing, the arm swing frequency obtained in real time in each of the vertical and horizontal directions is compared with the preset arm swing frequency in each of the vertical and horizontal directions, respectively. If the arm swing frequency obtained in real time in each direction matches the preset arm swing frequency in the corresponding direction, the exercise information is determined according to the moving body part corresponding to the matching preset arm swing frequency, thereby increasing accuracy of the determination result.

Figure 3:
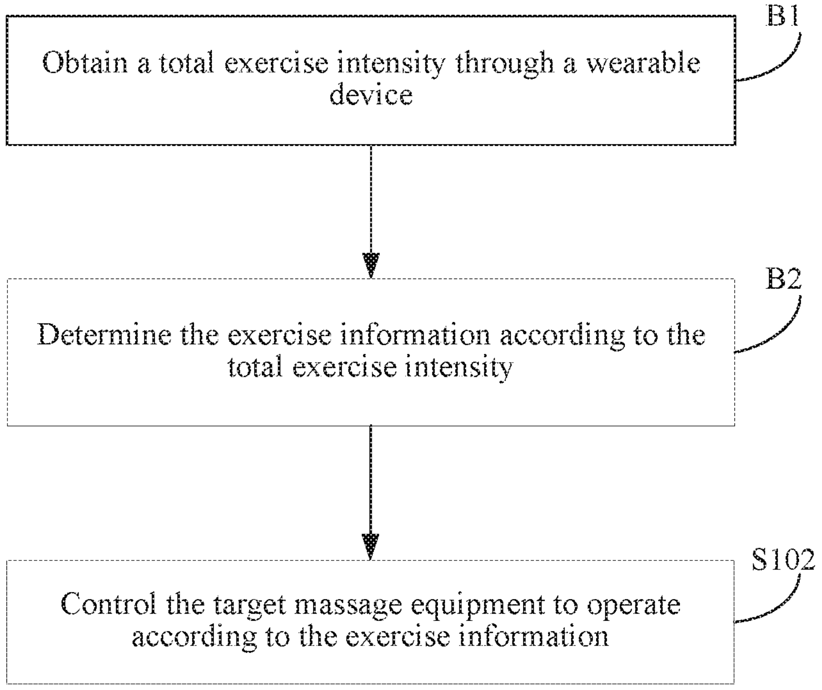
FIG. 3 shows another flowchart illustrating a method for obtaining exercise information according to another exemplary embodiment of the present disclosure.

FIG. 3 shows another flow chart illustrating a method of obtaining exercise information according to another exemplary embodiment of the present disclosure.

As shown in FIG. 3, the step S101 shown in FIG. 1 is executed as follows.

At step B1, a total exercise intensity is obtained through a wearable device. The total exercise intensity includes one or more of a pulse rate, a pulse intensity, a heartbeat frequency, and a heartbeat intensity when the user is exercising.

In some embodiments, the wearable device, such as a smart band and a smart watch, directly detects the pulse rate and the pulse intensity when the user is exercising. The heartbeat frequency and the heartbeat intensity of the user are obtained indirectly based on the pulse rate and the pulse intensity. Accordingly, the total exercise intensity when the user is exercising is obtained through the wearable device. In some embodiments, the wearable device is connected to the terminal or the target massage equipment through a communication method, such as Bluetooth, infrared technology, WiFi (Wireless Fidelity, e.g., wireless local area network based on IEEE 802.11 standards), etc. The total exercise intensity is transmitted to the terminal or the target massage equipment, such that the terminal or the target massage equipment is enabled to perform operations shown in the following steps B2 and B3.

At step B2, the exercise information is determined according to the total exercise intensity.

In some embodiments, after the total exercise intensity is obtained, the terminal or the target massage equipment automatically determines the current exercise information of the user according to the total exercise intensity. For example, in some embodiments, the exercise intensity ratio between various moving body parts and the exercise intensity information of each moving body part is determined with improved accuracy by combining with the moving body part information obtained based on the arm swing frequency. For example, when the user's moving body part is determined as the leg according to the arm swing frequency and the user is perhaps using a treadmill for jogging, the exercise intensities of upper limbs and lower limbs are determined according to the total exercise intensity. The exercise intensity ratio between the upper limbs and the lower limbs are further determined. Thus, the target massage equipment performs a targeted movement based on the exercise information when the user is exercising, so as to automatically provide a comfortable, suitable, and effective massage to the user based on the user's exercise information. Therefore, after exercise, the user's body can better recover through the optimum massage. The disclosed method may not require the user to manually select the massage mode, thereby reducing the user's operations.

Additionally, this embodiment can be combined with the previously discussed embodiment, in which the exercise information is determined according to the arm swing frequency obtained by the wearable device. Furthermore, this embodiment can be combined with the embodiment described below, in which information regarding exercise equipment used when the user is exercising is determined, so as to obtain more comprehensive and accurate exercise information.

Figure 4:
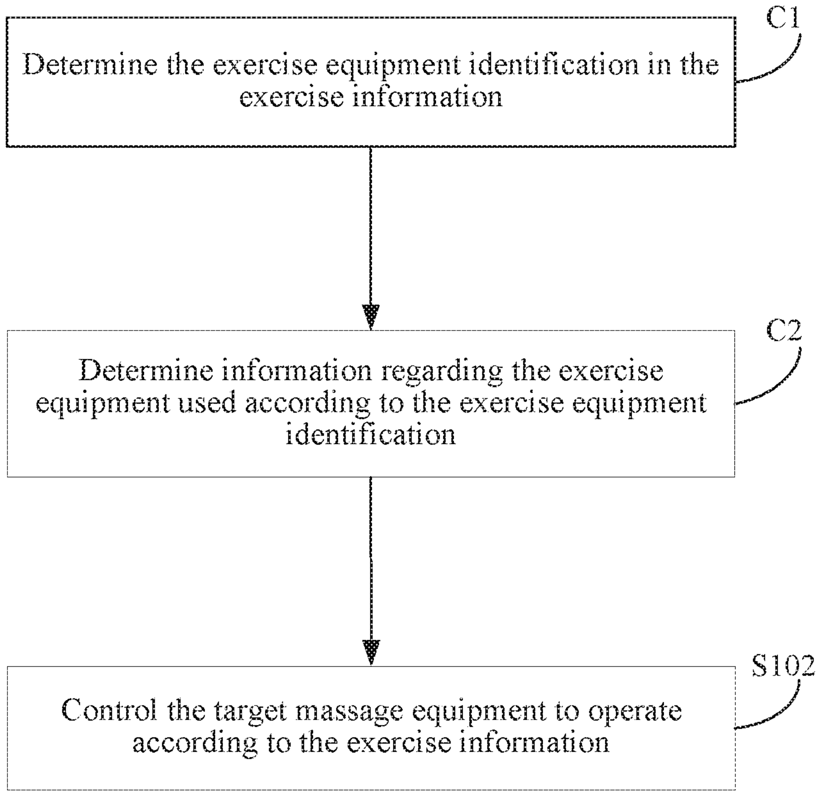
FIG. 4 shows yet another flowchart illustrating a method for obtaining exercise information according to yet another exemplary embodiment of the present disclosure.

FIG. 4 shows another flowchart illustrating another method for obtaining exercise information according to another exemplary embodiment of the present disclosure.

As shown in FIG. 4, the step S101 shown in FIG. 1 is executed as follows.

At step C1, an exercise equipment identification in the exercise information is determined.

In some embodiments, the terminal or the target massage equipment identifies the exercise information obtained by the wearable device. Then, the terminal or the target massage equipment determines the exercise equipment identification included in the exercise information. The specific method for obtaining the exercise equipment identification by the wearable device includes, but is not limited to, the following embodiments.

In one embodiment, the user manually inputs the exercise equipment identification of the exercise equipment used when the user is exercising into the wearable device, such as the smart band, the smart watch, etc., which is worn by the user.

Alternatively, in another embodiment, the user's current movement direction is automatically determined by an acceleration sensor or a direction sensor embedded in the wearable device, such as the smart band, the smart watch, etc., which is worn by the user. Then the exercise equipment identification is determined indirectly. For example, if the acceleration sensor or the direction sensor detects that the user's arm moves upwardly all the time, the exercise equipment identification is determined to be an identification of a dumbbell or a horizontal bar.

Alternatively, in yet another embodiment, if the exercise equipment used by the user is intelligent (such as having Bluetooth functionality), the exercise equipment identification is sent to the wearable device worn by the user, such as the smart band, the smart watch, etc., via the Bluetooth.

At step C2, information regarding the exercise equipment used is determined according to the exercise equipment identification. The information regarding the exercise equipment used includes at least one of a name of the exercise equipment or a working parameter of the exercise equipment.

In some embodiments, after the exercise equipment identification is determined by the terminal or the target massage equipment, information regarding the exercise equipment used when the user is exercising, such as the name of the exercise equipment, the working parameter of the exercise equipment (such as a movement rate of the treadmill if the exercise equipment used is a treadmill, or a weight of the dumbbell if the exercise equipment used is a dumbbell), etc., is determined according to the exercise equipment identification. Then, the target massage equipment is controlled to provide a targeted massage to the user according to the information regarding the exercise equipment used when the user is exercising, such that the user's body can recover from fatigue as soon as possible. As a result, the user's experience on the comfort level of the target massage equipment is improved.

Additionally, this embodiment can be combined with the previously described embodiment, in which the exercise information is determined according to the arm swing frequency obtained by the wearable device. Moreover, this embodiment can also be combined with the previously described embodiment, in which the exercise information is determined according to the obtained total exercise intensity, so as to obtain more comprehensive and accurate exercise information.

In an embodiment of the present disclosure, the exercise information includes at least one of the followings: moving body part information regarding a body part of the user that has been exercised, an exercise intensity ratio between moving body parts that have been exercised, exercise intensity information regarding the moving body parts, and information regarding the exercise equipment that have been used in the exercise.

In one embodiment, the exercise information includes, but is not limited to, at least one of the followings: the user's moving body part information, an exercise intensity ratio between moving body parts, exercise intensity information regarding the moving body parts, the information regarding the exercise equipment used in the exercise, and, a total exercise time of the user.

Figure 5:
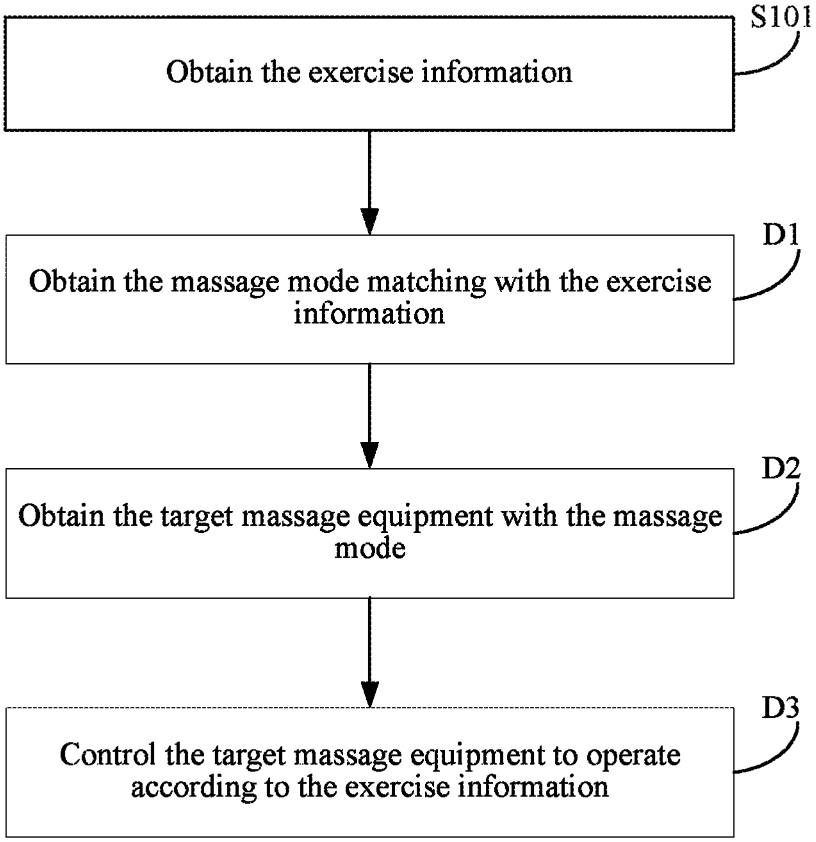
FIG. 5 shows a flowchart illustrating a method for controlling target massage equipment to operate according to exercise information, according to an exemplary embodiment of the present disclosure.

FIG. 5 shows a flowchart illustrating a method for controlling target massage equipment to operate according to exercise information, according to an exemplary embodiment of the present disclosure.

As shown in FIG. 5, the step S102 shown in FIG. 1 is executed as follows.

At step D1, a massage mode matching the exercise information is obtained.

When the target massage equipment is controlled to operate according to the exercise information for providing a targeted massage to a user, a massage mode matching the exercise information is first obtained. That is, the massage mode that matches the exercise information and that can help the user's body recover from the fatigue caused by the exercise as soon as possible is obtained. For example, if the exercise equipment used by the user is a treadmill, since the main moving body part is the legs and the legs perform a large amount of activity, the massage mode can be a foot massage mode, a leg massage mode, etc. If the exercise equipment used by the user is a dumbbell or a horizontal bar, since the main moving body part is the arms and the arms perform a large amount of activity, the massage mode can be an arm massage mode, a hand massage mode etc.

At step D2, the target massage equipment with the massage mode is obtained.

For example, when the massage mode is a foot massage mode, the target massage equipment can be a massage chair, a foot massager, a foot massage basin, etc.

At step D3, the target massage equipment is controlled to operate based on the massage mode.

In some embodiments, the target massage equipment with the massage mode is obtained. Then the target massage equipment is controlled to operate based on the massage mode so as to automatically provide a comfortable, suitable, and effective massage to the user based on the user's exercise information, such that the user's body can recover in a better and faster manner after the exercise through an optimum massage. The disclosed method may not require the user to manually select the massage mode, thereby reducing the user's operations.

In some embodiments, each massage mode has its corresponding preset massage parameter, and each user's specific exercise information is distinct. For example, when the same exercise equipment is used, the total exercise intensity, the exercise intensity of each body part, the exercise ratio, and the length of exercise time can vary. Accordingly, after the roughly matching massage mode is determined, the target massage equipment is controlled to operate as follows.

In some embodiments, the exercise information is compared with the preset exercise information corresponding to the massage mode.

In some embodiments, the preset massage parameter corresponding to the massage mode is adjusted according to the comparison result. The preset massage parameter includes one or more of a preset length of massage time and a preset massage intensity. For example, when the massage mode is an upper limb massage, and when the exercise intensity ratio between the upper limb and the lower limb in the exercise is higher than the preset exercise intensity ratio between the upper limb and the lower limb corresponding to the massage mode, the preset massage parameter corresponding to the massage mode is increased for increasing the massage time and intensity for the upper limb. When the exercise intensity ratio between the upper limb and the lower limb in the exercise is lower than the preset exercise intensity ratio between the upper limb and the lower limb corresponding to the massage mode, the preset massage parameter corresponding to the massage mode is decreased for decreasing the massage time and intensity for the upper limb. In this manner, the inherent preset massage parameter of the massage mode is adjusted according to the user's specific exercise information, so as to automatically provide a more intelligent targeted massage service to the user. Thus, the user's body can recover from exercise in a much better and faster manner, thereby improving the user's experience on the comfort level of the target massage equipment.

In an embodiment of the present disclosure, the massage mode includes a historical massage mode matching the exercise information.

In some embodiments, when determining the massage mode, it is not necessary to re-determine the mode every time. The exercise information of the user in each exercise and the determined matching massage mode are stored in relation to each other. Thus, when the user performs a subsequent exercise, if the determined exercise information is exactly the same as that in a previous exercise, or the difference is smaller than a predetermined threshold, it is not required to re-determine the massage mode suitable for the user. Instead, the historical massage mode matching the exercise information in the previous exercise is directly determined as the massage mode for the subsequent exercise, so as to avoid re-determination, thereby reducing user operations and the burden on the terminal and the target massage equipment.

Figure 6:
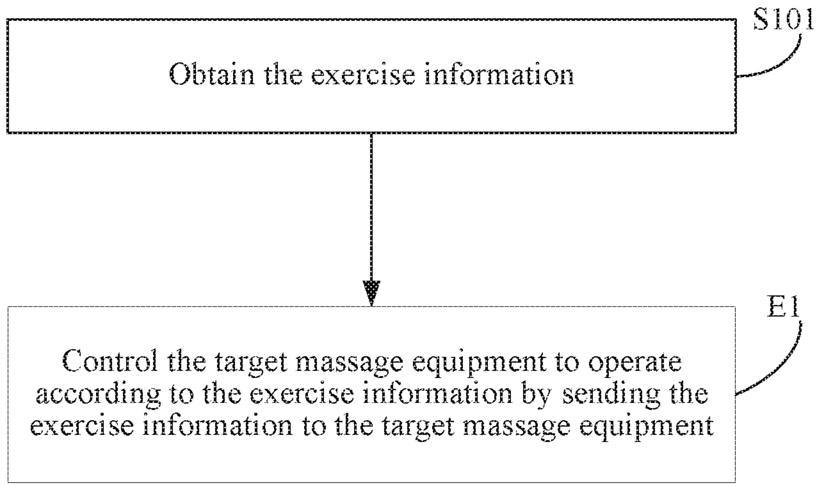
FIG. 6 shows another flowchart illustrating a method for controlling target massage equipment to operate according to exercise information, according to another exemplary embodiment of the present disclosure.

FIG. 6 shows another flowchart illustrating a method for controlling target massage equipment to operate according to exercise information, according to another exemplary embodiment of the present disclosure.

As shown in FIG. 6, the step S102 shown in FIG. 1 is executed as follows.

At step E1, the target massage equipment is controlled to operate according to the exercise information by sending the exercise information to the target massage equipment.

In some embodiments, when the subject that obtains the exercise information is a terminal and the target massage equipment is controlled to operate according to the exercise information, the terminal sends the obtained exercise information to the target massage equipment, and then controls the target massage equipment to operate according to the exercise information, such that the target massage equipment is automatically controlled through the terminal to provide a comfortable, suitable, and effective massage to the user based on the user's exercise information. Thus, after exercise, the user's body can better recover through an optimum massage. The disclosed method may not require the user to manually select the massage mode, thereby reducing the user's operations.

Figure 7:
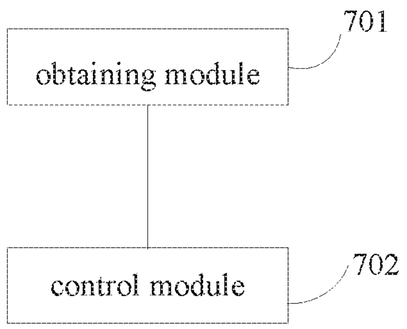
FIG. 7 is a block diagram of a device for controlling target massage equipment according to an exemplary embodiment of the present disclosure.

Corresponding to the above method for controlling target massage equipment, embodiments of the present disclosure also provide a device for controlling the target massage equipment. FIG. 7 is a block diagram of a device for controlling the target massage equipment according to an exemplary embodiment of the present disclosure.

As shown in FIG. 7, the device includes an obtaining module 701 and a control module 702.

The obtaining module 701 is configured to obtain exercise information.

The exercise information obtained by the obtaining module 701 is information obtained when the user is exercising at the present time. The exercise information includes, but is not limited to, at least one of the followings: the user's moving body part information, an exercise intensity ratio between moving body parts, exercise intensity information regarding the moving body parts, and information regarding exercise equipment used in the exercise.

Additionally, the subject that obtains the exercise information is a terminal or the target massage equipment.

The control module 702 is configured to control the target massage equipment to operate according to the exercise information obtained by the obtaining module 701. When the target massage equipment is controlled to operate according to the exercise information, the target massage equipment automatically provides personalized massage service to the user. Alternatively, in some embodiments, the target massage equipment is controlled to operate through the terminal so as to provide personalized massage service to the user.

In the disclosed embodiments, the exercise status of the user is determined with improved accuracy according to the obtained exercise information. Thus, the control module 702 controls the target massage equipment to perform a targeted movement based on the exercise information obtained when the user is exercising, so as to automatically provide a comfortable, suitable, and effective personalized massage to the user based on the user's exercise information. Therefore, after exercise, the user's body can recover much better through an optimum massage. The disclosed method may not require the user to manually select the massage mode, thereby reducing the user's operations.

Figure 8:
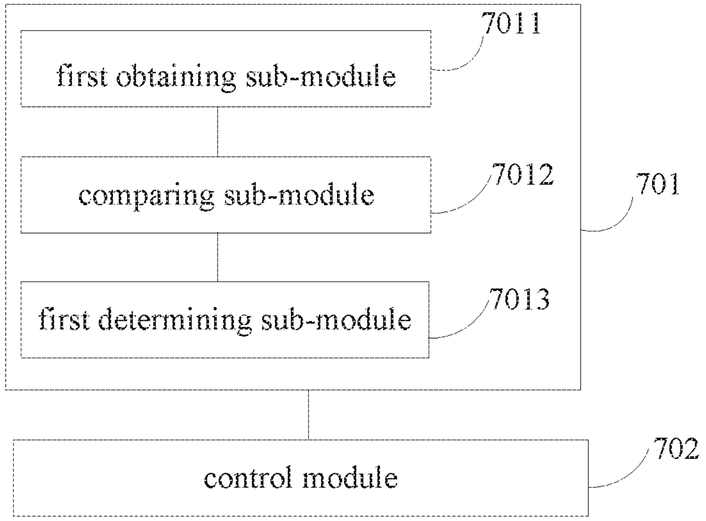
FIG. 8 is a block diagram of an obtaining module according to an exemplary embodiment of the present disclosure.

FIG. 8 is a block diagram of an obtaining module according to an exemplary embodiment of the present disclosure.

As shown in FIG. 8, the obtaining module 701 shown in FIG. 7 includes a first obtaining sub-module 7011, a comparing sub-module 7012, and a first determining sub-module 7013.

The first obtaining sub-module 7011 is configured to obtain an arm swing frequency through a wearable device. The wearable device includes at least one of a smart band or a smart watch.

Regardless of whether the exercise information is obtained by a terminal or the target massage equipment, the arm swing frequency can be obtained by the first obtaining sub-module 7011 through a wearable device. The wearable device is a smart band or a smart watch worn on a user's wrist. The wearable device can also be a smart band worn on a user's finger. The wearable device is connected to the terminal or the target massage equipment through a communication method, such as Bluetooth, infrared technology, or WiFi (Wireless Fidelity, e.g., wireless local area network based on IEEE 802.11 standards). Then the swing frequency is transmitted to the terminal or the target massage equipment, thereby enabling the terminal or the target massage equipment to perform operations.

The comparing sub-module 7012 is configured to compare the arm swing frequency obtained by the first obtaining sub-module 7011 with at least two preset arm swing frequencies.

The first determining sub-module 7013 is configured to determine the exercise information according to a moving body part corresponding to one of the at least two preset arm swing frequencies when the comparison result obtained by the comparing sub-module 7012 indicates that the arm swing frequency matches the one of the at least two preset arm swing frequencies.

Because each pre-stored preset arm swing frequency may correspond to a distinct moving body part (for example, when a user is lifting dumbbells, the arm swing frequency and the moving body part are different from those when the user is jogging), each preset arm swing frequency may correspond to distinct exercise information. Thus, it is judged whether the arm swing frequency obtained in real time matches one of the at least two preset arm swing frequencies by comparing the obtained arm swing frequency with the at least two preset arm swing frequencies using the comparing sub-module 7012. If the determination result of the first determining sub-module 7013 is that the arm swing frequency obtained in real time matches one of the at least two preset arm swing frequencies (for example, the arm swing frequency obtained in real time is equal to one of the at least two preset arm swing frequencies, or the difference between the two compared swing frequencies is less than or equal to a preset frequency threshold), it is determined that the exercise information corresponding to the arm swing frequency obtained in real time is the same as the exercise information based on the preset arm swing frequency matching the arm swing frequency obtained in real time. Therefore, the current exercise information of the user is determined according to the moving body part corresponding to the preset arm swing frequency matching the arm swing frequency obtained in real time. For example, the user's moving body part information or the like is determined according to the moving body part corresponding to the preset arm swing frequency matching the arm swing frequency obtained in real time.

Besides, because the arm swing frequency may not be a constant no matter what kind of equipment is used or what kind of exercise intensity is applied during the user's exercise or fitness activities, each of the at least two preset arm swing frequencies may have frequency fluctuation or may be represented by an arm swing frequency spectrogram. Correspondingly, the arm swing frequency obtained in real time may also have frequency fluctuation or may be represented by an arm swing frequency spectrogram. Thus, in some embodiments, when comparing, a similarity between two arm swing frequency spectrograms is obtained from the comparison. If the similarity is higher than a preset similarity (e.g. 90%), the exercise information is determined according to a preset swing frequency spectrogram with which the arm swing frequency obtained in real time has a similarity higher than the preset similarity.

Additionally, in some embodiments, each of the at least two preset arm swing frequencies includes an arm swing frequency in the vertical direction and an arm swing frequency in the horizontal direction. In such embodiments, when comparing, the arm swing frequency obtained in real time in each direction is compared respectively with the corresponding preset arm swing frequency in the corresponding direction. If the arm swing frequency in each direction matches the preset arm swing frequency respectively, the exercise information is determined according to the moving body part corresponding to the matching preset arm swing frequency, thereby increasing accuracy of the determination result.

Figure 9:
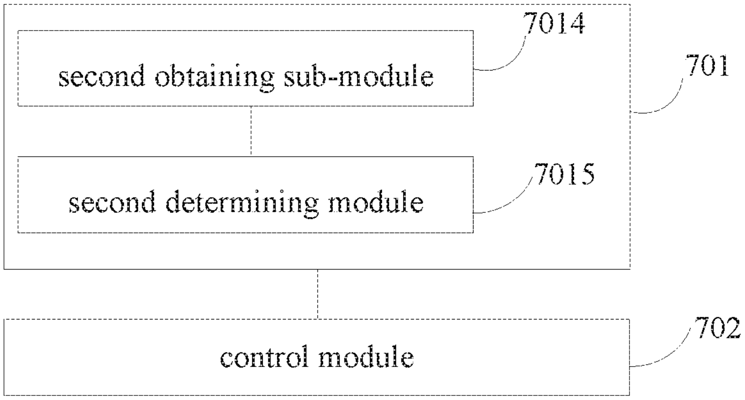
FIG. 9 is a block diagram of another obtaining module according to another exemplary embodiment of the present disclosure.

FIG. 9 is a block diagram of another obtaining module according to another exemplary embodiment of the present disclosure.

As shown in FIG. 9, the obtaining module 701 shown in FIG. 7 includes a second obtaining sub-module 7014 and a second determining sub-module 7015.

The second obtaining sub-module 7014 is configured to obtain a total exercise intensity through a wearable device. The total exercise intensity includes one or more of a pulse rate, a pulse intensity, a heartbeat frequency, and a heartbeat intensity when the user is exercising.

In some embodiments, the wearable device, such as a smart band or a smart watch, directly detects the pulse rate and the pulse intensity when the user is exercising. Then the heartbeat frequency and the heartbeat intensity of the user are obtained indirectly based on the pulse rate and the pulse intensity, such that the second obtaining sub-module 7014 obtains through the wearable device the total exercise intensity when the user is exercising. Further, in some embodiments, the wearable device is connected to the terminal or the target massage equipment through a communication method, such as Bluetooth, infrared technology, or WiFi (Wireless Fidelity, e.g., wireless local area network based on IEEE 802.11 standards). Then the total exercise intensity is transmitted to the terminal or the target massage equipment, thereby enabling the terminal or the target massage equipment to perform operations.

The second determining sub-module 7015 is configured to determine the exercise information according to the total exercise intensity obtained by the second obtaining sub-module 7014.

After the total exercise intensity is obtained by the second obtaining sub-module 7014, the second determining sub-module 7015 in the terminal or the target massage equipment automatically determines the current exercise information of the user according to the total exercise intensity. For example, in some embodiments, the exercise intensity ratio between moving body parts and the exercise intensity information regarding the moving body parts are determined with improved accuracy by combining with the moving body part information obtained based on the arm swing frequency. For example, after the user's moving body part is determined as the legs according to the arm swing frequency and the user is perhaps using a treadmill for jogging, the exercise intensities of upper limbs and lower limbs are determined according to the total exercise intensity. The exercise intensity ratio between the upper limbs and the lower limbs is further determined. Thus, the target massage equipment performs a targeted movement based on the exercise information obtained when the user is exercising, so as to automatically provide a comfortable, suitable, and effective massage to the user based on the user's exercise information. Therefore, after exercise, the user's body can recover much better through an optimum massage. The disclosed method may not require the user to manually select the massage mode, thereby reducing the user's operations.

Additionally, this embodiment can be combined with the previously described embodiment, in which the exercise information is determined according to the arm swing frequency obtained by the wearable device. Alternatively, this embodiment can also be combined with the embodiment described below, in which information regarding the exercise equipment used when the user is exercising is determined, so as to obtain more comprehensive and accurate exercise information.

Figure 10:
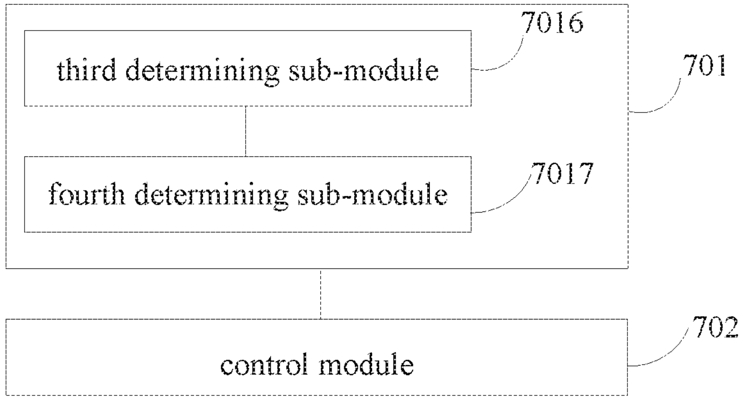
FIG. 10 is a block diagram of yet another obtaining module according to yet another exemplary embodiment of the present disclosure.

FIG. 10 is a block diagram of another obtaining module according to an exemplary embodiment of the present disclosure.

As shown in FIG. 10, the obtaining module 701 shown in FIG. 7 includes a third determining sub-module 7016 and a fourth determining sub-module 7017.

The third determining sub-module 7016 is configured to determine an exercise equipment identification in the exercise information.

In some embodiments, the third determining sub-module 7016 in the terminal or the target massage equipment identifies the exercise information obtained by the wearable device. Then, the third determining sub-module 7016 determines the exercise equipment identification included in the exercise information. The specific method for obtaining the exercise equipment identification by the wearable device includes, but is not limited to, the following embodiments.

In one embodiment, the user manually inputs the exercise equipment identification of the exercise equipment used when the user is exercising into the wearable device, such as the smart band, the smart watch, etc., worn by the user.

Alternatively, in another embodiment, the user's current movement direction is automatically determined by an acceleration sensor or a direction sensor embedded in the wearable device, such as the smart band, the smart watch, etc., worn by the user. Then the exercise equipment identification is determined indirectly. For example, if the acceleration sensor or the direction sensor detects that the user's arm moves upwardly all the time, the exercise equipment identification is determined as an identification of a dumbbell or a horizontal bar.

Alternatively, in yet another embodiment, if the exercise equipment used by the user used is relatively intelligent (such as having Bluetooth functionality), the exercise equipment identification is sent to the wearable device worn by the user, such as the smart band, the smart watch, etc., via the Bluetooth.

The fourth determining sub-module 7017 is configured to determine information regarding the exercise equipment used in the exercise according to the exercise equipment identification determined by the third determining sub-module 7016. The information regarding the exercise equipment used in the exercise includes at least one of a name of the exercise equipment or a working parameter of the exercise equipment.

In some embodiments, after the exercise equipment identification is determined by the third determining sub-module 7016 in the terminal or the target massage equipment, the fourth determining sub-module 7017 determines the information regarding the exercise equipment used when the user is exercising, such as the name of the exercise equipment and/or the working parameter of the exercise equipment (such as a movement rate of the treadmill if the used exercise equipment is a treadmill, or a weight of the dumbbell if the used exercise equipment is a dumbbell). Then, the target massage equipment is controlled to provide a targeted massage to the user based on the information regarding the exercise equipment used when the user is exercising, such that the user's body can recover from fatigue as soon as possible. As a result, the user's experience on the comfort level of the target massage equipment is improved.

Additionally, this embodiment can be combined with the previously described embodiment, in which the exercise information is determined according to the arm swing frequency obtained by the wearable device. Alternatively, this embodiment can be combined with the previously described embodiment, in which the exercise information is determined according to the obtained total exercise intensity, so as to obtain more comprehensive and accurate exercise information.

In one embodiment, the exercise information includes at least one of the followings: moving body part information, an exercise intensity ratio between moving body parts, exercise intensity information regarding the moving body parts, and information regarding exercise equipment used in the exercise.

In another embodiment, the exercise information includes, but is not limited to, at least one of the followings: moving body part information of the user, an exercise intensity ratio between moving body parts, exercise intensity information regarding the moving body parts, the information regarding the exercise equipment used in the exercise, and a total exercise time of the user.

Figure 11:
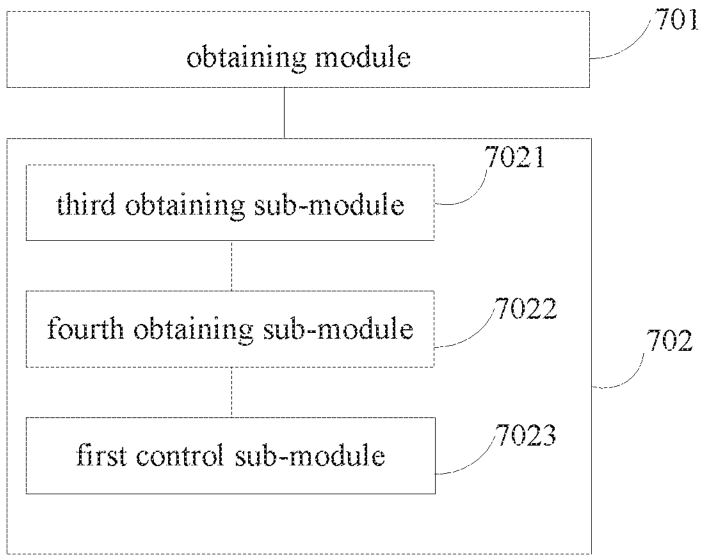
FIG. 11 is a block diagram of a control module according to an exemplary embodiment of the present disclosure.

FIG. 11 is a block diagram of a control module according to an exemplary embodiment of the present disclosure.

As shown in FIG. 11, the control module 702 shown in FIG. 7 includes a third obtaining sub-module 7021, a fourth obtaining sub-module 7022, and a first control sub-module 7023.

The third obtaining sub-module 7021 is configured to obtain a massage mode matching the exercise information obtained by the obtaining module 701.

In some embodiments, when the target massage equipment is controlled to operate according to the exercise information for providing a targeted massage for a user, a massage mode matching the exercise information is first obtained through the third obtaining sub-module 7021. That is, a massage mode that matches the exercise information and that helps the user's body recover from the fatigue caused by the exercise as soon as possible is obtained. For example, if the exercise equipment used by the user is a treadmill, since the main moving body part is the legs and the legs perform a large amount of activity, the massage mode can be a foot massage mode, a leg massage mode, etc. If the exercise equipment used by the user is a dumbbell or a horizontal bar, since the main moving body part is the arms and the arms perform a large amount of activity, the massage mode can be an arm massage mode, a hand massage mode, etc.

The fourth obtaining sub-module 7022 is configured to obtain the target massage equipment with the massage mode obtained by the third obtaining sub-module 7021.

In some embodiments, when the massage mode is a foot massage mode, the target massage equipment can be a massage chair, a foot massager, a foot massage basin, etc.

The first control sub-module 7023 is configured to control the target massage equipment obtained by the fourth obtaining sub-module 7022 to operate based on the massage mode.

In some embodiments, the target massage equipment with the massage mode is obtained by the fourth obtaining sub-module 7022. Then the target massage equipment is controlled by the first control sub-module 7023 to operate based on the massage mode so as to automatically provide a comfortable, suitable, and effective massage to the user based on the user's exercise information, such that after exercise the user's body can recover in a better and faster manner through an optimum massage. The disclosed method may not require the user to manually select the massage mode, thereby reducing the user's operations.

In some embodiments, each massage mode has its corresponding preset massage parameter, and each user's specific exercise information is distinct. For example, when the same exercise equipment is used in the exercise, the total exercise intensity, the exercise intensity of each body part, the exercise ratio, and the length of exercise time can vary. After the roughly matching massage mode is determined, the target massage equipment is controlled to operate as follows.

In some embodiments, the exercise information is compared with the preset exercise information corresponding to the massage mode.

In some embodiments, the preset massage parameter corresponding to the massage mode is adjusted according to the comparison result. The preset massage parameter includes one or more of a preset length of massage time and a preset massage intensity. For example, when the massage mode is upper limb massage, and the exercise intensity ratio between the upper limb and the lower limb in the exercise is higher than the preset exercise intensity ratio between the upper limb and the lower limb corresponding to the massage mode, the preset massage parameter corresponding to the massage mode is increased for increasing the massage time and intensity for the upper limb. When the exercise intensity ratio between the upper limb and the lower limb in the present exercise is lower than the preset exercise intensity ratio between the upper limb and the lower limb corresponding to the massage mode, the preset massage parameter corresponding to the massage mode is decreased for decreasing the massage time and intensity for the upper limb. In this way, the inherent preset massage parameter of the massage mode is adjusted according to user's specific exercise information, so as to automatically provide a more intelligent targeted massage service to the user. As a result, the user's body can recover from exercise in a much better and faster manner, thereby improving the user's experience on the comfort level of the target massage equipment.

In one embodiment, the massage mode includes a historical massage mode matching the exercise information.

In some embodiments, when determining the massage mode, it is not necessary to re-determine the mode every time. The exercise information of the user in each exercise and the determined matching massage mode are stored in relation to each other. Thus, when the user performs subsequent exercise, if the determined exercise information is the same as that in a previous exercise, or the difference is smaller than a predetermined threshold, it is not required to re-determine the massage mode suitable for the user. Instead, the historical massage mode matching the exercise information in the previous exercise is directly determined as the massage mode for the subsequent exercise, so as to avoid re-determination, thereby reducing the operations by the user and the burden on the terminal and the target massage equipment.

Figure 12:
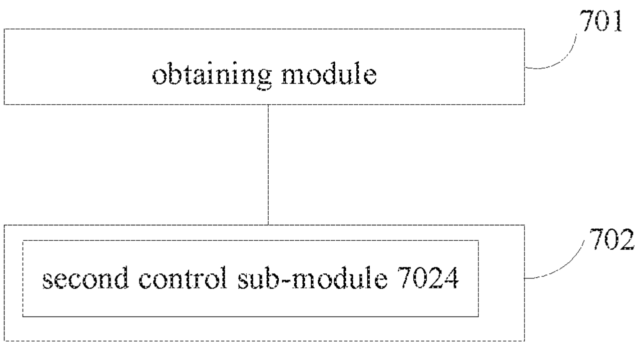
FIG. 12 is a block diagram of another control module according to another exemplary embodiment of the present disclosure.

FIG. 12 is a block diagram of another control module according to an exemplary embodiment of the present disclosure.

As shown in FIG. 12, the control module 702 shown in FIG. 7 includes a second control sub-module 7024.

The second control sub-module 7024 is configured to control the target massage equipment to operate according to the exercise information by sending the exercise information to the target massage equipment.

In some embodiments, when the subject that obtains the exercise information is a terminal and the target massage equipment is controlled to operate according to the exercise information, the second control sub-module 7024 in the terminal sends the obtained exercise information to the target massage equipment. The second control sub-module 7024 then controls the target massage equipment to operate according to the exercise information, such that the target massage equipment is automatically controlled through the terminal to provide a comfortable, suitable, and effective massage to the user based on the user's exercise information. Thus, after exercise, the user's body can recover much better through an optimum massage. The disclosed method may not require the user to manually select the massage mode, thereby reducing the user's operations.

According to one aspect of the present disclosure, a device for controlling target massage equipment is provided. The device includes a processor, and a memory for storing an instruction executable by the processor. The processor is configured to execute the instructions to obtain exercise information and control the target massage equipment to operate according to the exercise information.

In some embodiments, the processor is further configured to obtain exercise information by obtaining an arm swing frequency through a wearable device. The wearable device includes at least one of a smart band or a smart watch. The processor obtains the exercise information also by comparing the arm swing frequency with at least two preset arm swing frequencies. If the arm swing frequency matches one of the at least two preset arm swing frequencies, the processor determines the exercise information according to a moving body part corresponding to the one of the at least two preset arm swing frequencies.

In some embodiments, the processor is also configured to obtain exercise information by obtaining a total exercise intensity through a wearable device when a user is exercising. The total exercise intensity includes one or more of a pulse rate, a pulse intensity, a heartbeat frequency, and a heartbeat intensity when the user is exercising. The processor also obtains the exercise information by determining the exercise information according to the total exercise intensity.

In some embodiments, the processor is also configured to obtain exercise information by determining an exercise equipment identification in the exercise information, and by determining information regarding exercise equipment used in the exercise according to the exercise equipment identification. The information regarding the exercise equipment used in the exercise includes at least one of a name of the exercise equipment used or a working parameter of the exercise equipment used.

In some embodiments, the exercise information includes at least one of the following: moving body part information, an exercise intensity ratio between moving body parts, exercise intensity information regarding the moving body parts, and information regarding exercise equipment used in the exercise.

In some embodiments, the processor is also configured to control the target massage equipment to operate according to the exercise information, by obtaining a massage mode matching the exercise information, obtaining the target massage equipment with the massage mode, and controlling the target massage equipment to operate based on the massage mode.

In some embodiments, the massage mode includes a historical massage mode matching the exercise information.

In some embodiments, the processor is also configured to control the target massage equipment to operate according to the exercise information by sending the exercise information to the target massage equipment.

Figure 13:
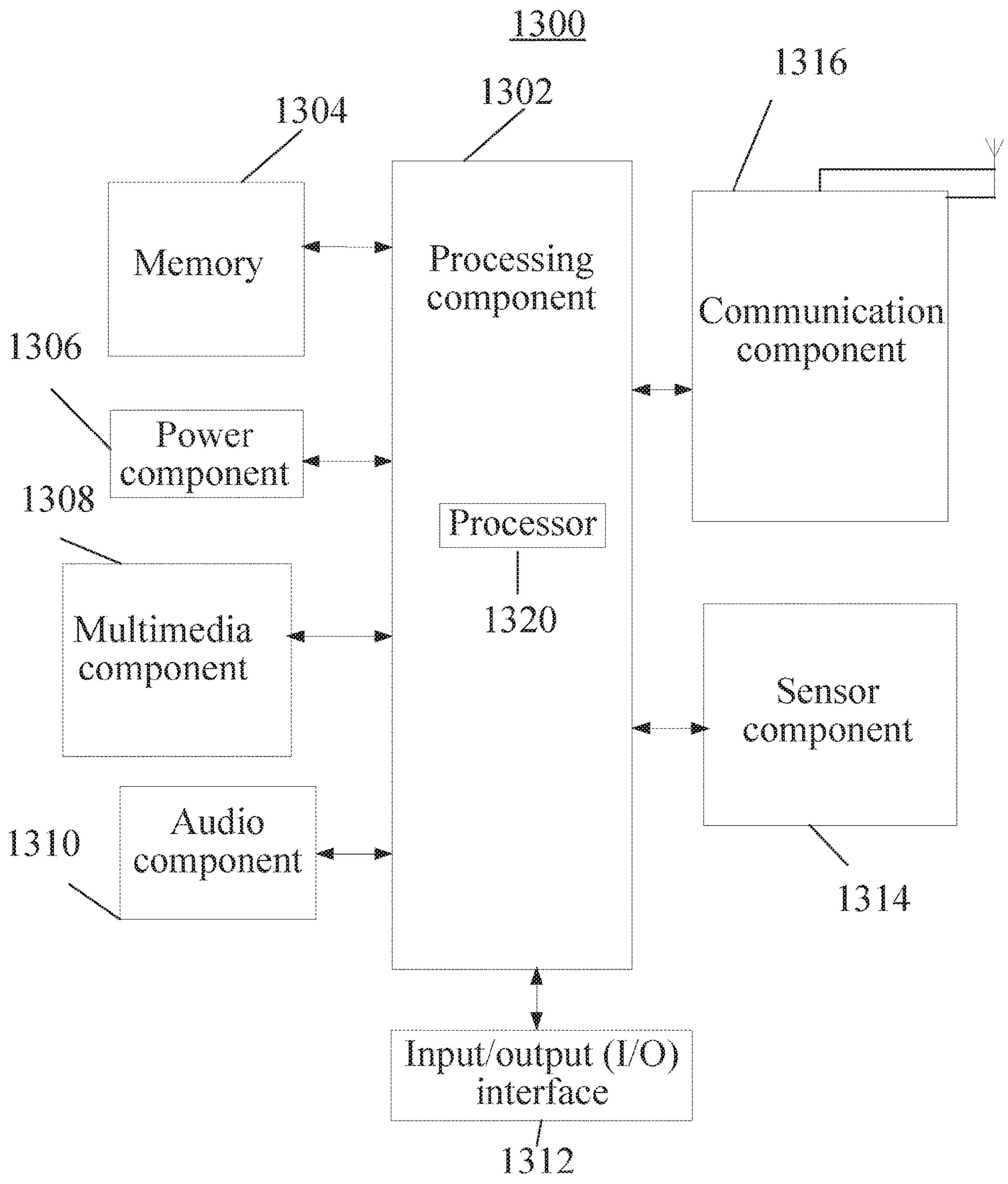
FIG. 13 is a block diagram of a device for controlling target massage equipment according to an exemplary embodiment of the present disclosure.

FIG. 13 is a block diagram of a device 1300 for controlling target massage equipment according to an exemplary embodiment of the present disclosure. The device 1300 is applied in a terminal. For example, the device 1300 can be a mobile phone, a computer a digital broadcast terminal, a messaging device, a gaming console, a tablet, a medical device, an exercise equipment, a personal digital assistant, or the like. In some embodiments, the device 1300 may also be implemented in the target massage equipment.

Referring to FIG. 13, the device 1300 includes at least one of the following components: a processing component 1302, a memory 1304, a power component 1306, a multimedia component 1308, an audio component 1310, an input/output (I/O) interface 1312, a sensor component 1314, and a communication component 1316.

The processing component 1302 is configured to control the overall operations of the device 1300, such as the operations associated with display, telephone calls, and data communications, camera operations, and recording operations. The processing component 1302 includes at least one processor 1320 configured to execute instructions to perform all or part of the disclosed methods. Moreover, the processing component 1302 includes at least one module that facilitates the interaction between the processing component 1302 and other components. For example, the processing component 1302 includes a multimedia module configured to facilitate the interaction between the multimedia component 1308 and the processing component 1302.

The memory 1304 is configured to store various types of data to support the operation of the device 1300. Examples of such data include instructions for any applications or methods operated on the device 1300, contact data, phonebook data, messages, pictures, video, etc. The memory 1304 can be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 1306 provides power to various components of the device 1300. The power component 1306 includes a power management system, one or more power sources, and any other components associated with the generation, management, and distribution of power in the device 1300.

The multimedia component 1308 includes a screen providing an output interface between the device 1300 and the user. The screen may include a liquid crystal display and a touch panel. If the screen includes the touch panel, the screen is implemented as a touch screen to receive input signals from the user. The touch panel includes one or more touch sensors to sense touches, swipes, and gestures on the touch panel. The touch sensors not only sense a boundary of a touch or swipe action, but also sense a period of time and a pressure associated with the touch or swipe action. In some embodiments, the multimedia component 1308 includes a front camera and/or a rear camera. The front camera and/or the rear camera receive an external multimedia datum while the device 1300 is in an operation mode, such as a photographing mode or a video mode. Each of the front camera and the rear camera has a fixed optical lens system or has focus and optical zoom capability.

The audio component 1310 is configured to output and/or input audio signals. For example, the audio component 1310 includes a microphone configured to receive an external audio signal when the device 1300 is in an operation mode, such as a call mode, a recording mode, and a voice recognition mode. The received audio signal is further stored in the memory 1304 or transmitted via the communication component 1316. In some embodiments, the audio component 1310 further includes a speaker configured to output audio signals.

The I/O interface 1312 provides an interface between the processing component 1302 and peripheral interface modules, such as a keyboard, a click wheel, buttons, and the like. The buttons may include, but are not limited to, a home button, a volume button, a starting button, and a locking button.

The sensor component 1314 includes at least one sensor configured to provide status assessments of various aspects of the device 1300. For example, the sensor component 1314 detects an open/closed status of the device 1300, relative positioning of components, e.g., the display and the keypad, of the device 1300, a change in position of the device 1300 or a component of the device 1300, presence or absence of user's contact with the device 1300, an orientation or an acceleration/deceleration of the device 1300, and a change in temperature of the device 1300. In some embodiments, the sensor component 1314 includes a proximity sensor configured to detect the presence of nearby objects without any physical contact. In some embodiments, the sensor component 1314 also includes a light sensor, such as a CMOS or CCD image sensor, for use in imaging applications. In some embodiments, the sensor component 1314 also includes an accelerometer sensor, a gyroscope sensor, a magnetic sensor, a pressure sensor, or a temperature sensor.

The communication component 1316 is configured to facilitate wired or wirelessly communication between the device 1300 and other devices. The device 1300 can access a wireless network based on a communication standard, such as WiFi, 2G, 3G, 4G, or a combination thereof. In one embodiment, the communication component 1316 receives a broadcast signal or broadcast associated information from an external broadcast management system via a broadcast channel. In one embodiment, the communication component 1316 further includes a near field communication (NFC) module configured to facilitate short-range communications. For example, the NFC module may be implemented based on a radio frequency identification (RFID) technology, an infrared data association (IrDA) technology, an ultra-wideband (UWB) technology, a Bluetooth (BT) technology, or other suitable technologies.

In some embodiments, the device 1300 is implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the disclosed methods.

In some embodiments, there is also provided a non-transitory computer-readable storage medium including instructions, such as instructions included in the memory 1304, executable by the processor 1320 in the device 1300, for performing the disclosed methods. For example, the non-transitory computer-readable storage medium can be a ROM, a RAM, a CD-ROM, a magnetic tape, a floppy disc, an optical data storage device, and the like.

In some embodiments, there is also provided a non-transitory computer-readable storage medium having stored therein instructions that, when executed by a processor, cause the device 1300 to perform a method for controlling target massage equipment. The method includes obtaining exercise information and controlling the target massage equipment to operate according to the exercise information.

In some embodiments, obtaining exercise information includes obtaining an arm swing frequency through a wearable device, wherein the wearable device includes at least one of a smart band or a smart watch; comparing the arm swing frequency with at least two preset arm swing frequencies; and when the arm swing frequency matches one of the at least two preset arm swing frequencies, determining the exercise information according to a moving body part corresponding to the one of the at least two preset arm swing frequencies.

In some embodiments, obtaining exercise information includes obtaining a total exercise intensity through a wearable device when a user is exercising, wherein the total exercise intensity includes one or more of a pulse rate, a pulse intensity, a heartbeat frequency, and a heartbeat intensity when the user is doing exercise; and determining the exercise information according to the total exercise intensity.

In some embodiments, obtaining exercise information includes determining an exercise equipment identification in the exercise information; and determining information regarding exercise equipment used in the exercise according to the exercise equipment identification. The information regarding the exercise equipment used in the exercise includes at least one of a name of the exercise equipment used in the exercise or a working parameter of the exercise equipment used in the exercise.

In some embodiments, the exercise information includes at least one of moving body part information, an exercise intensity ratio between moving body parts, exercise intensity information regarding the moving body parts, or information regarding exercise equipment used in the exercise.

In some embodiments, controlling the target massage equipment to operate according to the exercise information includes obtaining a massage mode matching the exercise information; obtaining the target massage equipment with the massage mode; and controlling the target massage equipment to operate based on the massage mode.

In some embodiments, the massage mode includes a historical massage mode matching the exercise information.

In some embodiments, controlling the target massage equipment to operate according to the exercise information includes sending the exercise information to the target massage equipment.

Other embodiments of the present disclosure will be apparent to those skilled in the art from consideration of the specification and practice of the disclosure disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A method for controlling target massage equipment, comprising:

obtaining, by a processor, an arm swing frequency and a total exercise intensity when a user is doing exercise through a wearable device;

obtaining, by the processor, exercise information according to the arm swing frequency and the total exercise intensity;

controlling, by the processor, the target massage equipment to operate according to the exercise information;

comparing the arm swing frequency with at least two preset arm swing frequencies; and if the arm swing frequency matches one of the at least two preset arm swing frequencies, determining the exercise information according to a moving body part corresponding to the one of the at least two preset arm swing frequencies, the wearable device comprising at least one of a smart band and a smart watch worn on the user's wrist or finger and configured to obtain the arm swing frequency of the user.

2. The method according to claim 1, wherein obtaining exercise information according to the total exercise intensity includes:

determining the exercise information according to the total exercise intensity, the total exercise intensity comprising one or more of a pulse rate, a pulse intensity, a heartbeat frequency, and a heartbeat intensity when the user is doing exercise.

3. The method according to claim 2, wherein controlling the target massage equipment to operate according to the exercise information includes:

obtaining a massage mode matching the exercise information;

obtaining the target massage equipment with the massage mode; and controlling the target massage equipment to operate based on the massage mode.

4. The method according to claim 1, wherein obtaining exercise information includes:

determining an exercise equipment identification in the exercise information; and determining information regarding exercise equipment used in exercise according to the exercise equipment identification, wherein the information regarding the exercise equipment used in the exercise includes at least one of a name of the exercise equipment or a working parameter of the exercise equipment.

5. The method according to claim 4, wherein controlling the target massage equipment to operate according to the exercise information includes:

obtaining a massage mode matching the exercise information;

obtaining the target massage equipment with the massage mode; and controlling the target massage equipment to operate based on the massage mode.

6. The method according to claim 1, wherein the exercise information includes at least one of moving body part information, an exercise intensity ratio between moving body parts, exercise intensity information regarding the moving body parts, or information regarding exercise equipment used in the exercise.

7. The method according to claim 1, wherein controlling the target massage equipment to operate according to the exercise information includes:

obtaining a massage mode matching the exercise information;

obtaining the target massage equipment with the massage mode; and controlling the target massage equipment to operate based on the massage mode.

8. The method according to claim 7, wherein the massage mode includes a historical massage mode containing information matching the exercise information.

9. The method according to claim 2, wherein controlling the target massage equipment to operate according to the exercise information includes:

obtaining a massage mode matching the exercise information;

obtaining the target massage equipment with the massage mode; and controlling the target massage equipment to operate based on the massage mode.

10. The method according to claim 1, wherein controlling the target massage equipment to operate according to the exercise information includes:

controlling the target massage equipment to operate according to the exercise information by sending the exercise information to the target massage equipment.

11. A device for controlling target massage equipment, comprising:

a memory for storing instructions; and a processor configured to execute the instructions to:

obtain an arm swing frequency and a total exercise intensity when a user is doing exercise through a wearable device;

obtain exercise information according to the arm swing frequency and the total exercise intensity;

control the target massage equipment to operate according to the exercise information;

compare the arm swing frequency with at least two preset arm swing frequencies; and determine the exercise information according to a moving body part corresponding to one of the at least two preset arm swing frequencies when the arm swing frequency matches the one of the at least two preset arm swing frequencies, the wearable device comprising at least one of a smart band or a smart watch worn on the user's wrist or finger and configured to obtain the arm swing frequency of the user.

12. The device according to claim 11, wherein the processor is configured to obtain exercise information according to the total exercise intensity by:

determining the exercise information according to the total exercise intensity, the total exercise intensity comprising one or more of a pulse rate, a pulse intensity, a heartbeat frequency, and a heartbeat intensity when the user is doing exercise.

13. The device according to claim 11, wherein the processor is configured to obtain exercise information by:

determining an exercise equipment identification in the exercise information; and determining information regarding exercise equipment used in exercise according to the exercise equipment identification, wherein the information of the exercise equipment used in the exercise includes at least one of a name of the exercise equipment used or a working parameter of the exercise equipment used.

14. The device according to claim 11, wherein the exercise information includes at least one of: moving body part information, an exercise intensity ratio between moving body parts, exercise intensity information regarding the moving body parts, or information regarding exercise equipment used in the exercise.

15. The device according to claim 11, wherein the processor is configured to control the target massage equipment to operate according to the exercise information by:

obtaining a massage mode matching the exercise information;

obtaining the target massage equipment with the massage mode; and controlling the target massage equipment to operate based on the massage mode.

16. The device according to claim 15, wherein the massage mode includes a historical massage mode containing information matching the exercise information.

17. The device according to claim 11, wherein the processor is configured to control the target massage equipment to operate according to the exercise information by:

controlling the target massage equipment to operate according to the exercise information by sending the exercise information to the target massage equipment.

18. A non-transitory computer readable storage medium having instructions stored therein that, when executed by one or more processors of a device, cause the device to perform a method for controlling target massage equipment, the method comprising:

obtaining an arm swing frequency and a total exercise intensity when a user is doing exercise through a wearable device;

obtaining exercise information according to the arm swing frequency and the total exercise intensity;

controlling the target massage equipment to operate according to the exercise information;

comparing the arm swing frequency with at least two preset arm swing frequencies; and determining the exercise information according to a moving body part corresponding to one of the at least two preset arm swing frequencies when the arm swing frequency matches the one of the at least two preset arm swing frequencies, the wearable device comprising at least one of a smart band or a smart watch worn on the user's wrist or finger and configured to obtain the arm swing frequency of the user.

* * * * *